(12) United States Patent
Poucher et al.

(10) Patent No.: US 9,717,443 B2
(45) Date of Patent: *Aug. 1, 2017

(54) SURGICAL TOOL AND METHOD FOR IDENTIFYING AN INCISION SITE

(71) Applicant: Coloplast A/S, Humlebaek (DK)

(72) Inventors: Neal Poucher, North Oaks, MN (US); Fernando El-Hage, Brooklyn Park, MN (US); Deborah Kidder, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 440 days.

This patent is subject to a terminal disclaimer.

(21) Appl. No.: 14/314,038

(22) Filed: Jun. 25, 2014

(65) Prior Publication Data

US 2015/0359454 A1 Dec. 17, 2015

Related U.S. Application Data

(63) Continuation of application No. 14/302,465, filed on Jun. 12, 2014.

(51) Int. Cl.
*A61B 5/05* (2006.01)
*A61B 5/06* (2006.01)
*A61F 2/00* (2006.01)
A61B 17/00 (2006.01)
A61B 17/32 (2006.01)
A61B 90/00 (2016.01)

(52) U.S. Cl.
CPC ............ *A61B 5/065* (2013.01); *A61B 90/39* (2016.02); *A61F 2/0004* (2013.01); *A61B 2017/00292* (2013.01); *A61B 2017/320052* (2013.01); *A61B 2090/3945* (2016.02); *A61B 2090/3958* (2016.02)

(58) Field of Classification Search
USPC ........................................................ 600/409
See application file for complete search history.

(56) References Cited

U.S. PATENT DOCUMENTS

| | | | |
|---|---|---|---|
| 3,744,063 | A | 7/1973 | McWhorter et al. |
| 4,063,548 | A | 12/1977 | Klatt et al. |
| | | (Continued) | |

FOREIGN PATENT DOCUMENTS

| | | |
|---|---|---|
| EP | 2662041 A2 | 11/2013 |
| EP | 2666423 A1 | 11/2013 |
| | (Continued) | |

OTHER PUBLICATIONS

AMS 800 Urinary Control System, Operating Room Manual, Mar. 2004.

*Primary Examiner* — Joel F Brutus
(74) *Attorney, Agent, or Firm* — Coloplast Corp., Coloplast A/S; Nick Baumann (57) ABSTRACT

A method of identifying a site for a perineal incision on a patient includes inserting a distal end portion of an intra-urethral probe into a urethra of the patient, and guiding the distal end portion of the intra-urethral probe along a length of the urethra no farther than a junction in the urethra. The method additionally includes transmitting a signal from the distal end portion of the intra-urethral probe through the urethra, and sensing the signal at a location on a perineal skin surface, where the location correlates with the junction in the urethra.

18 Claims, 11 Drawing Sheets

(56) References Cited

U.S. PATENT DOCUMENTS

| | | | |
|---|---|---|---|
| 4,191,196 A | 3/1980 | Bradley et al. | |
| 4,222,377 A | 9/1980 | Burton | |
| 4,412,530 A | 11/1983 | Burton | |
| 4,878,889 A | 11/1989 | Polyak | |
| 4,909,785 A | 3/1990 | Burton et al. | |
| 4,932,956 A | 6/1990 | Reddy et al. | |
| 4,932,958 A | 6/1990 | Reddy et al. | |
| 4,994,020 A | 2/1991 | Polyak | |
| 5,007,898 A | 4/1991 | Rosenbluth et al. | |
| 5,078,720 A | 1/1992 | Burton et al. | |
| 5,335,669 A | 8/1994 | Tihon et al. | |
| 5,356,423 A | 10/1994 | Tihon et al. | |
| 5,423,321 A | 6/1995 | Fontenot | |
| 5,496,271 A | 3/1996 | Burton et al. | |
| 5,499,994 A | 3/1996 | Tihon et al. | |
| 5,518,504 A | 5/1996 | Polyak | |
| 5,720,415 A | 2/1998 | Morningstar | |
| 5,895,356 A | 4/1999 | Andrus et al. | |
| 5,911,715 A * | 6/1999 | Berg | A61M 25/0009 138/125 |
| 5,971,967 A * | 10/1999 | Willard | A61M 25/04 600/29 |
| 6,382,214 B1 | 5/2002 | Raz et al. | |
| 6,460,262 B1 | 10/2002 | Cabak et al. | |
| 6,540,665 B1 | 4/2003 | Connolly | |
| 6,558,315 B1 | 5/2003 | Kuyava | |
| 6,612,977 B2 | 9/2003 | Staskin et al. | |
| 6,616,653 B2 | 9/2003 | Beyar et al. | |
| 6,652,450 B2 | 11/2003 | Neisz et al. | |
| 6,802,807 B2 | 10/2004 | Anderson et al. | |
| 6,971,986 B2 | 12/2005 | Staskin et al. | |
| 7,015,253 B2 | 3/2006 | Escandon et al. | |
| 7,048,682 B2 | 5/2006 | Neisz et al. | |
| 7,083,568 B2 | 8/2006 | Neisz et al. | |
| 7,267,645 B2 | 9/2007 | Anderson et al. | |
| 7,291,104 B2 | 11/2007 | Neisz et al. | |
| 7,315,762 B2 | 1/2008 | Mosher et al. | |
| 2004/0106845 A1 | 6/2004 | Anderson et al. | |
| 2004/0204734 A1 | 10/2004 | Wagner et al. | |
| 2006/0036164 A1 | 2/2006 | Wilson et al. | |
| 2006/0122493 A1 | 6/2006 | Atalar et al. | |
| 2007/0083080 A1* | 4/2007 | Kim | A61H 21/00 600/102 |
| 2007/0255291 A1 | 11/2007 | Brock et al. | |
| 2008/0194973 A1 | 8/2008 | Imam | |
| 2009/0270791 A1* | 10/2009 | Todd | A61B 17/32002 604/22 |
| 2010/0016844 A1 | 1/2010 | Patel, Jr. | |
| 2010/0240952 A1 | 9/2010 | Okazaki et al. | |
| 2012/0123243 A1 | 5/2012 | Hastings | |
| 2013/0090554 A1* | 4/2013 | Zvuloni | A61B 10/0241 600/424 |
| 2013/0345718 A1* | 12/2013 | Crawford | A61B 17/025 606/130 |

FOREIGN PATENT DOCUMENTS

| | | |
|---|---|---|
| SE | 529191 C2 | 5/2007 |
| WO | 2005086739 A2 | 9/2005 |
| WO | 2011076211 A1 | 6/2011 |

* cited by examiner

SURGICAL TOOL AND METHOD FOR IDENTIFYING AN INCISION SITE

BACKGROUND

Urinary incontinence affects many people and is a worldwide health issue. Published research indicates that urinary incontinence presents a substantial social and economic burden worldwide, affecting up to a mean of about 16% of the global population.

Urinary incontinence in women can be associated with a prolapse of one or more pelvic organs, which can arise from child birth or a weakness in the tissues/muscle of the pelvic floor. Urinary incontinence in men can arise after surgical treatment of the prostate glade, which treatment can include removal or weakening of the prostatic sphincter of the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

One aspect provides a surgical tool adapted for identifying an incision site. The surgical tool includes an intra-urethral probe and a transmitter. The intra-urethral probe has a distal end opposite of a proximal end. A distal end portion of the intra-urethral probe is insertable into a urethra of a patient and is sized and configured to prevent the distal end of the intra-urethral probe from entering a bladder of the patient. The transmitter is located at the distal end portion of the intra-urethral probe and is configured to transmit a signal from inside of the urethra to an exterior surface of skin of the patient where the signal is sensed. The signal transmitted is one of a magnetic field, a vibratory pulse, a sound, or light in a visible wavelength.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this application may be combined with each other ("mixed and matched"), unless specifically noted otherwise.

Soft tissue includes dermal tissue, sub-dermal tissue, ligaments, tendons, or membranes but does not include bone.

The term "anterior" in this application means front, as in forward, and the term "posterior" means back, as in rearward. For example, the chin is anterior and the shoulder blade is posterior on the human anatomy.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the prostate of the patient.

A surgical tool has a distal end that is insertable into a urethra of a patient, as taken in reference to the surgeon handling a proximal end of the tool.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

Artificial urinary sphincters have proved useful in the treatment of urinary incontinence. An artificial urinary sphincter is implanted around the urethra and is operable to selectively coapt the lumen of the urethra to allow the user to shift the artificial sphincter from an open state that allows urine to pass to a closed state that provides the user with a continence.

Figure 1:
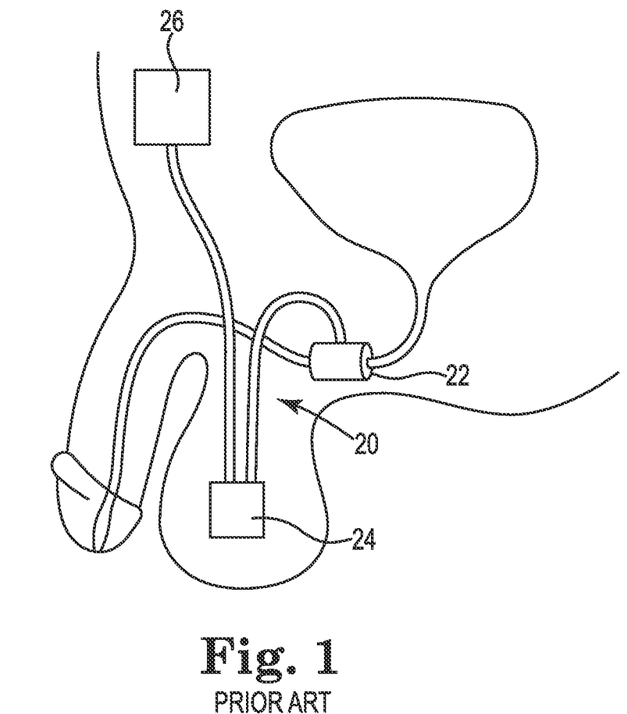
FIG. 1 is a perspective view of a prior art artificial urinary sphincter (AUS) system implanted in a male patient.

FIG. 1 is a perspective view of a prior art artificial urinary sphincter (AUS) system 20 implanted in the urogenital region of a male patient. The AUS system 20 includes three components cooperatively attached with tubing: an occlusive cuff 22, a control pump 24, and a pressure-regulating balloon reservoir 26. The cuff 22 is implanted around the urethra. The control pump 24 is implanted in the scrotum of a male user. The pressure-regulating balloon reservoir 26 is implanted in the prevesical space, for example somewhere in the abdomen.

During implantation of the AUS 20, the surgeon will generally form a perineal incision to access the urethra distal of the bladder. Tissue is dissected around the circumference of the urethra to create a space that allows for the placement of the cuff 22 around the urethra.

The male anatomy includes a bend or a junction in the urethra where the urethra transitions from a horizontal orientation extending generally along the length of the penis to a vertical orientation that connects with the bladder. Each man can have a slightly different location for the bend in the urethra. Surgeons prefer to place the cuff of an AUS near the bend in the urethra or immediately distal to the bend in the urethra as this location (referred to as the bulbar urethra) is associated with favorable muscle mass around the urethra.

Embodiments provide a kit of parts and a system that is useful for identifying an incision site in the perineum of a male patient, where the incision site is located on the skin at or immediately distal the bend in the urethra, where the bend is identified by a tool as described below. Forming an incision at the located incision site allows the surgeon improved and more accurate access to the bulbar urethra, with less dissection of tissue.

Embodiments provide a surgical system adapted for consistently and repeatably identifying the natural bend in the urethra for each individual patient. After the natural bend in the urethra is identified the surgeon will access that targeted area through an incision formed in the perineal skin.

Embodiments provide a surgical system adapted for identifying an incision site for the placement of an AUS. The system includes an intra-urethral probe having a distal end that is insertable into a urethra of a patient and a transmitter that transmits a signal from inside of the urethra to an exterior surface of skin of the patient where the signal is sensed. Sensing the signal on the exterior surface of the skin allows the surgeon to mark (with a pen or a marker) the desired location for making the incision.

Figure 2:
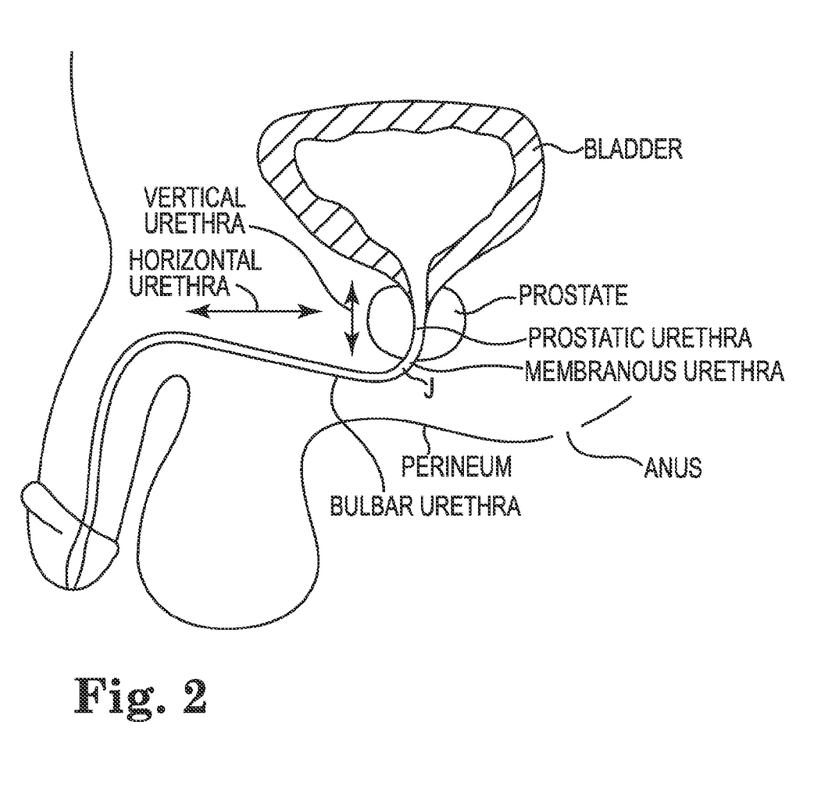
FIG. 2 is a schematic view of male anatomy and one embodiment of a kit of parts including a surgical tool adapted for identifying an incision site.

FIG. 2 is a schematic view of one embodiment of a kit 30 of parts providing instructions 32 for use of a surgical tool 34 adapted for identifying an incision site in the male anatomy. The instructions 32 for use provides the healthcare facility or healthcare person with direction from the manufacturer as to the regulatory-approved use of the surgical tool 34. The surgical tool 34 (tool 34) includes a handle 36 attached to an intra-urethral probe 38 (probe 38).

It is desirable to place the cuff of an AUS around that portion of the horizontal urethra that is closest to the junction J, in part because this section of the anatomy is where the most muscle mass resides in relation to the urethra. Some patients have had all or a portion of their prostate removed. Removal of the prostate can weaken or diminish the functionality of the sphincter located in the prostatic urethra. The prostatic urethra is located in that section of the urethra that descends in a vertical orientation away from the bladder, and the prostatic urethra may or may not include a functioning sphincter. The bulbar urethra is located in that section of the urethra that extends in a horizontal orientation away from the location of the prostate or prostatic urethra. The horizontal section of the bulbar urethra extends to the pendulous urethra that exits the penis.

The surgeon desires to place the cuff of the AUS around the bulbar urethra immediately distal a junction J where the vertical prostatic urethra bends and transitions to the horizontal bulbar urethra. In other words, the surgeon desires to place the cuff of the AUS at the bulbar urethra immediately distal the prostatic urethra (and at or immediately distal the junction J). Locating this junction in the urethra is a challenge. Specifically, locating the site on the perineum to form the incision to access the bulbar urethra presents a challenge to some surgeons, as the location of the bend associated with the horizontal/vertical junction J of the urethra is somewhat different for each individual.

The probe 38 is rigid, and sized and shaped to be inserted a distance in the horizontal section of the urethra until arriving at the junction J where urethra bends or transitions to its vertical orientation. The probe 38 does not bend along the urethra as would an intermittent or other form of urinary catheter, and thus the probe 38 cannot and does not enter the bladder. Instead, when inserted, a distal-most end the probe 38 (the end that is away from the handle 36) travels into the urethra until the urethra bends, at which point the probe 38 can no longer advance. This location of the most proximal advancement of the distal end 52 of the probe 38 indicates the location of the junction J where the urethra transitions from the horizontal orientation to the vertical orientation.

The probe 38 is unable to bend or navigate the transition in the curvature of the junction J of the urethra. The probe 38 is provided with a transmitter that broadcasts or transmits or radiates a signal from inside the urethra to the exterior surface of the skin to mark the location on the perineal skin that corresponds with the location of the distal-most end of the probe 38. The surgeon follows this mark to identify the location on the perineal skin in determining the incision site for implantation of the AUS.

Figure 3:
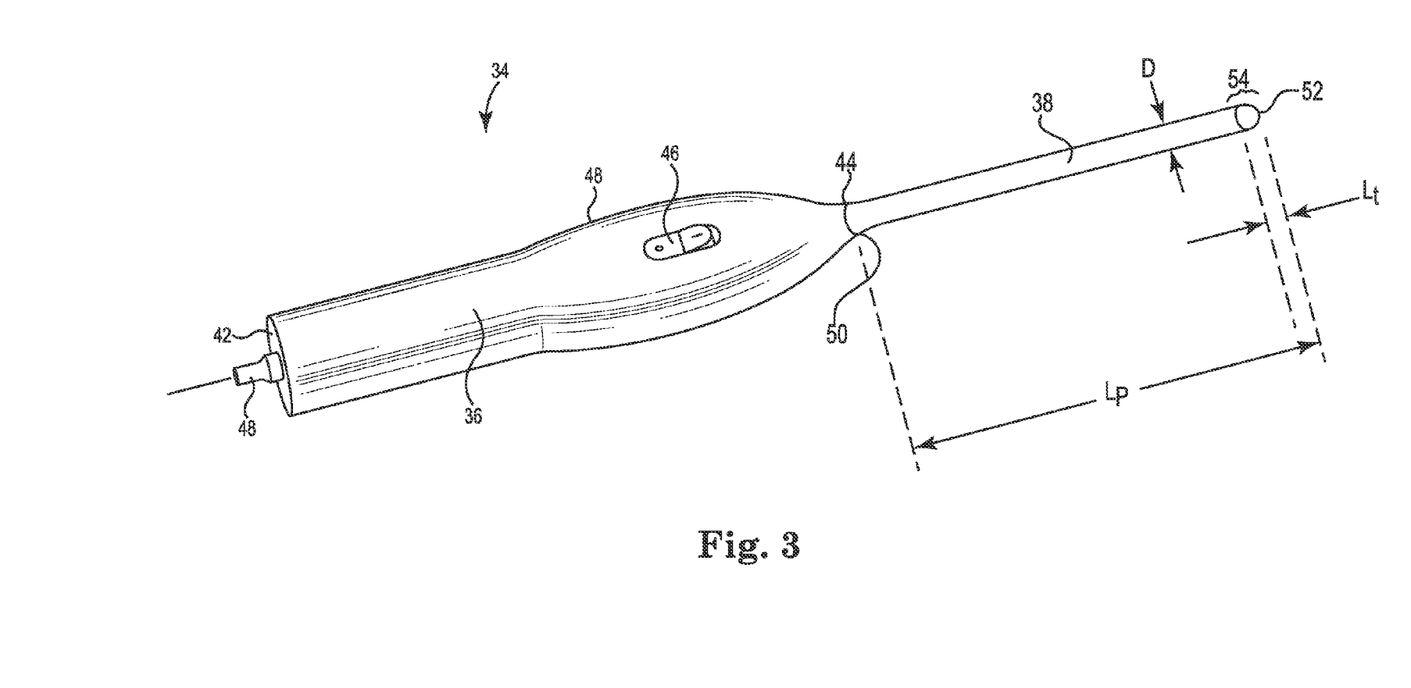
FIG. 3 is a perspective view of one embodiment of a surgical tool adapted for identifying an incision site.

FIG. 3 is a perspective view of the tool 34 with the handle 36 supporting the probe 38. The handle 36 includes a grip 40 located between a proximal end 42 and a distal end 44, where the grip 40 provides an ergonomic surface that reduces or eliminates the occurrence of twisting of the tool 34 within the surgeon's hand. The handle 36 includes a switch 46 that toggles between an off position and an on position. The on position energizes the probe 38. The switch 46 communicates with a connector 48 that is attached to the proximal end 42 of handle 36, where the connector 48 is connectable to a source of energy that drives the transmission of a signal from the probe 38 in response to movement of the switch 46.

The handle 36 is fabricated from metal or plastic. One suitable approach for fabricating the handle 36 includes molding a top half and a bottom half of the handle 36. Joining the top half of the handle to the bottom half of the handle forms a housing that encloses the switch components in the circuitry of the tool 34.

The probe 38 extends between a proximal end 50 and a distal end 52. A distal end portion 54 of the probe 38 is provided with a transmitter (several of which are described below) that is connected to the switch 46 and the connector 48. The transmitter is fabricated to transmit a magnetic field, a vibratory pulse, a sound or sound wave, or visible light through the tissue of the urethra and the perineum to be sensed or received at a surface of the skin.

The distal end 52 of the probe 38 is sized to be insertable into the urethra of the patient up to the location of the junction J (FIG. 2). The probe 38 is configured to resist bending in a manner that prevents the distal end 52 from entering a bladder of the patient. That is to say, the probe 38 lacks the flexibility to follow the bend in the urethra that transitions from the horizontal section of the urethra to the vertical section of the urethra. The probe 38 has a rigidity that is selected to prevent the probe 38 from bending, and in combination with the size of the probe 38, this prevents the distal end 52 of the probe 38 from traversing the curved portion of the urethra.

The probe 38 has a length Lp extending from the proximal end 50 to the distal end 52, where the length Lp is selected to be less than a length of the male urethra, for example less than about 16 cm. One approach includes fabricating the probe 38 to have a length of about 10 mm that is shorter than most male urethras to ensure that the distal end 52 of the probe 38 cannot enter the bladder of the patient.

In one embodiment, the distal end portion 54 of the probe 38 extends a distance Lt in a proximal direction from the distal end 52, where Lt is less than about 25% of the length Lp of the probe 38. The distal end portion 54 of the probe 38 houses or maintains the signal transmitter. It is desirable to configure the distal end portion 54 in a manner that will "pinpoint" a location of the distal end 52 of the inserted probe 38 since the distal end 52 extends into the urethra only so far as the junction J (FIG. 2). In some embodiments, the distance Lt of the distal end portion 54 of the probe 38 is less than about 15% of the length Lp of the probe 38, or between 1-10% of the length Lp of the probe 38, and preferably the distance Lt of the distal end portion 54 of the probe is between 1-5% of the length Lp of the probe 38.

The probe 38 is provided with a diameter D that is small enough to allow the probe 38 to be inserted into the urethra and large enough to prevent the probe 38 from traversing the curvature in a urethra (at the junction J of the urethra) and entering the bladder. In one embodiment, the diameter D of the probe 38 is in a range from 5-15 mm and is sized to prevent the distal end 52 of the probe 38 from entering the bladder of the patient.

The flexural modulus is a ratio of measured stress to strain during a flexing deformation. The flexural modulus characterizes the tendency of a material to bend. The flexural modulus is determined from the slope of the stress-strain curve produced during a flexural test, such as provided for and described in standard test ASTM D 790. The units of flexural modulus is force per area represented as pounds per square inch (psi). In one embodiment, the probe 38 has a rigidity selected to prevent the probe 38 from bending along the curvature of the urethra. In one embodiment, the probe 38 has a flexural modulus of greater than 50,000 psi. One suitable range for the flexural modulus of the probe 38 is between 50,000-250,000 psi, with one suitable flexural modulus being about 100,000 psi. As comparative examples, polyethylene has a flexural modulus of about 101,500 psi and polypropylene flexural modulus of about 217,500 psi. Flexural moduli above 250,000 psi are acceptable as this material will be stiffer and more resistant to bending, which will contribute to preventing the probe 38 from advancing past the curved portion of the urethra leading to the bladder.

Suitable materials for the fabrication of the probe 38 include stainless steel, a high density polyethylene, polypropylene, or a coated polymer sheath over a stainless steel rod. In one embodiment, a hydrophilic coating is applied to the probe 38 to provide a lubricious surface having reduced friction when in contact with the urethral tissue.

Figures 4A, 4B, 4C:
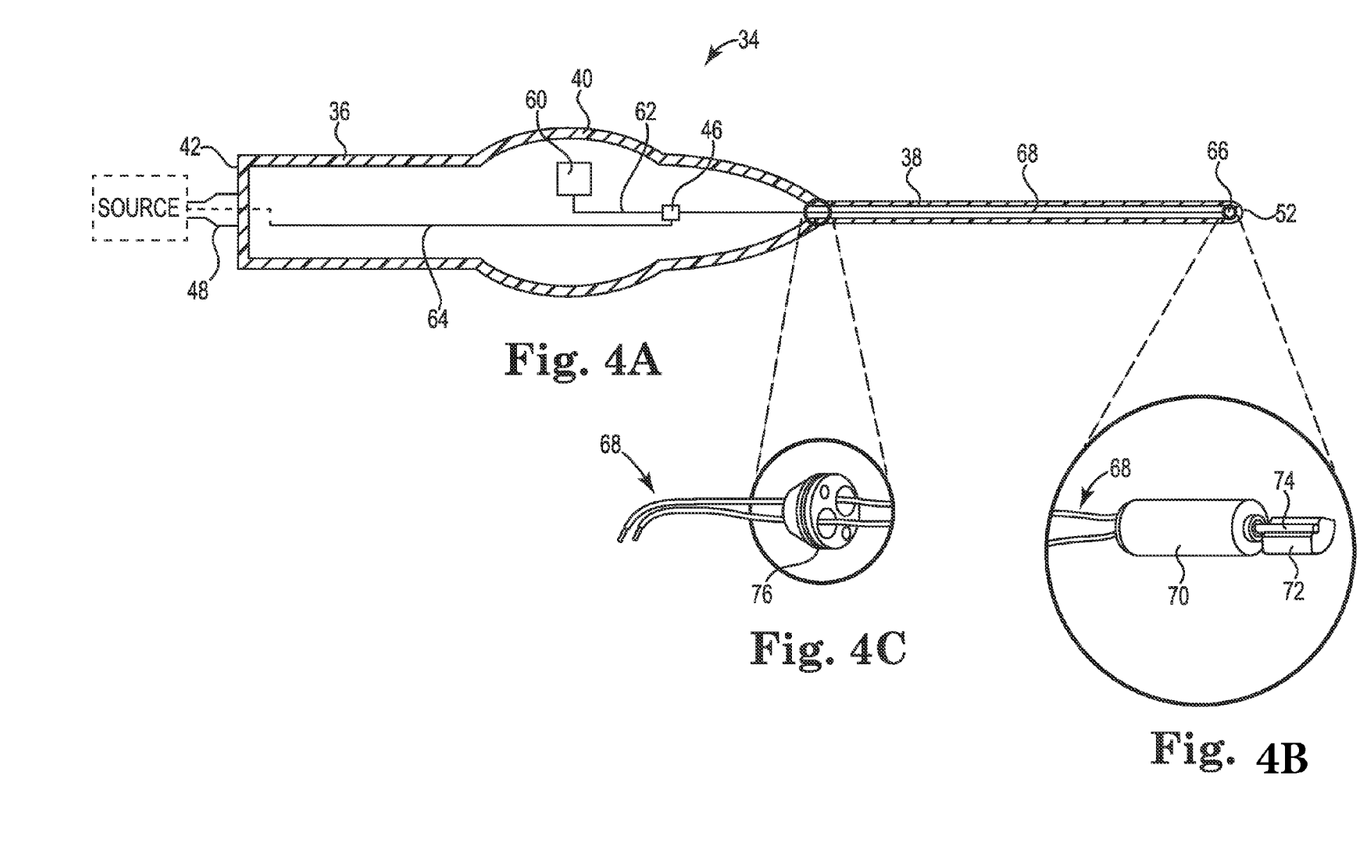
FIG. 4A is a cross-sectional view of the surgical tool illustrated in FIG. 3 provided with one embodiment of a transmitter.
FIG. 4B is a perspective view of the transmitter illustrated in FIG. 4A.
FIG. 4C is a perspective view of a seal associated with the transmitter illustrated in FIG. 4B.

FIG. 4A is a cross-sectional view of the tool 34. The interior of the handle 36 retains components of the switch 46 that are electrically connected to an integrated circuit 60 by a first electrical connection 62, and to the connector 48 and the energy source by a second electrical connection 64, and to a transmitter 66 by a third electrical connection 68. In one embodiment, the transmitter 66 is a vibratory transmitter.

FIG. 4B is a perspective view of the vibratory transmitter 66. In one embodiment, the transmitter 66 is an encapsulated vibration motor 70 having a coreless design that is retained within the distal end portion 54 of the probe 38. One suitable motor 70 is a miniaturized, low-voltage DC vibrating motor. The transmitter 66 is sealed within the probe 38 to reduce or prevent the ingress of water, dust, or other undesirable debris. The transmitter 66 has no external moving parts, as the moving parts are retained within the probe 38.

The electrical connection 68 is electrically connected to the switch 46 (FIG. 3) and its circuitry 60. Operation of the switch 46 causes a balance weight 72 to rotate on the axis of shaft 74. Rotation of the balance weight 72 causes a vibratory output since the balance weight 72 has a non-uniform distribution of mass relative to the shaft 74. In other words, the motor 70 vibrates as the out-of-balance weight 72 rotates around the shaft 74. One suitable output for the transmitter 66 is a vibratory pulse in a range from 1-100 Hz, for example at a frequency from 4 to 16 Hz, which is controlled by the rotational rate of the shaft 74.

FIG. 4C illustrates one embodiment of a seal 76 that is connected between the probe 38 and the handle 36 to organize and seal the electrical connection 68 and the motor 70 in a waterproof manner within the tool 34.

Suitable vibratory motors are available from, for example, Precision Microdrives™ at the Internet address http://www.precisionmicrodrives.com/.

Figure 5:
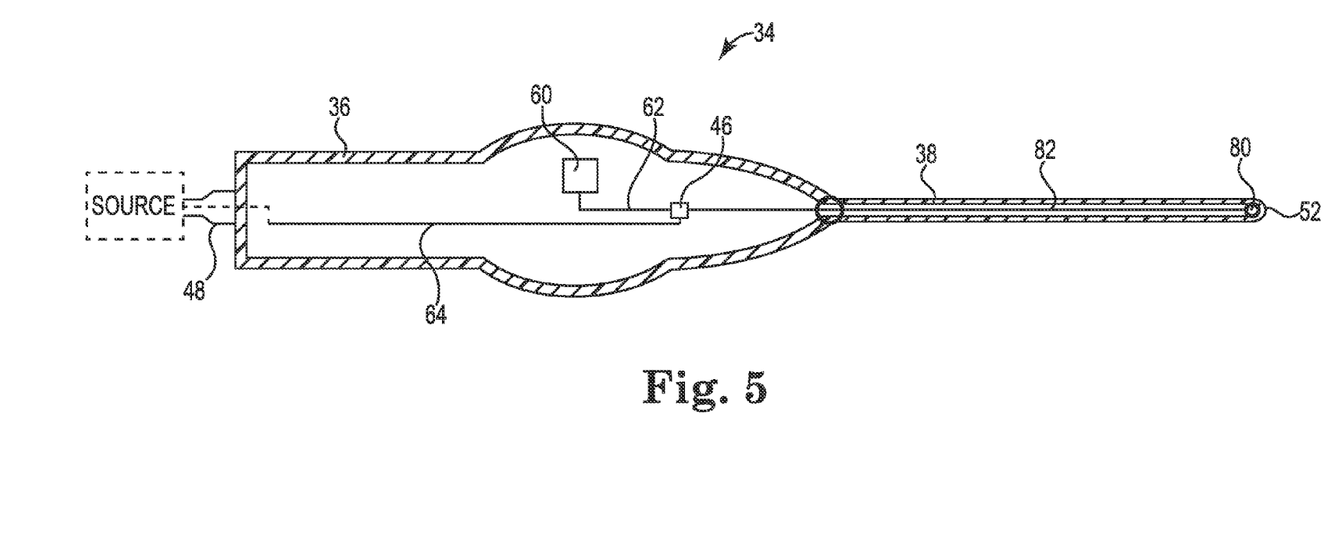
FIG. 5 is a cross-sectional view of the surgical tool illustrated in FIG. 3 provided with one embodiment of a transmitter.

FIG. 5 is a cross-sectional view of one embodiment of the tool 34. The switch 46 is appropriately connected to the integrated circuit 60 by the electrical connection 62 and to a transmitter 80 by electrical connection 82. In one embodiment, the transmitter 80 is configured to transmit a sound signal through a driven speaker, where the speaker is energized by the electrical connection 64 connected to an electrical source.

In one embodiment, the transmitter 80 is provided as a miniature-style of speaker referred to as a Mylar™ speaker having an impedance of about 8 ohms with a rated power of less than 1 watt. The speaker is sized to fit longitudinally on the axis of the probe 38, and is desirably sealed against moisture and debris ingress to the probe 38. It is desirable to provide an output sound in the aural range of the human ear, from about 20-20,000 Hz, although few ears are able to sense sound at the lowest frequency range. In one embodiment, the transmitter 80 operates to provide an output signal, or sound, in a frequency range from 1800-7000 Hz. Suitable such speakers for the transmitter 80 are available from Mallory Sonalert Products, Inc. through Digi-Key Corporation, Thief River Falls, Minn.

Figures 6A, 6B:
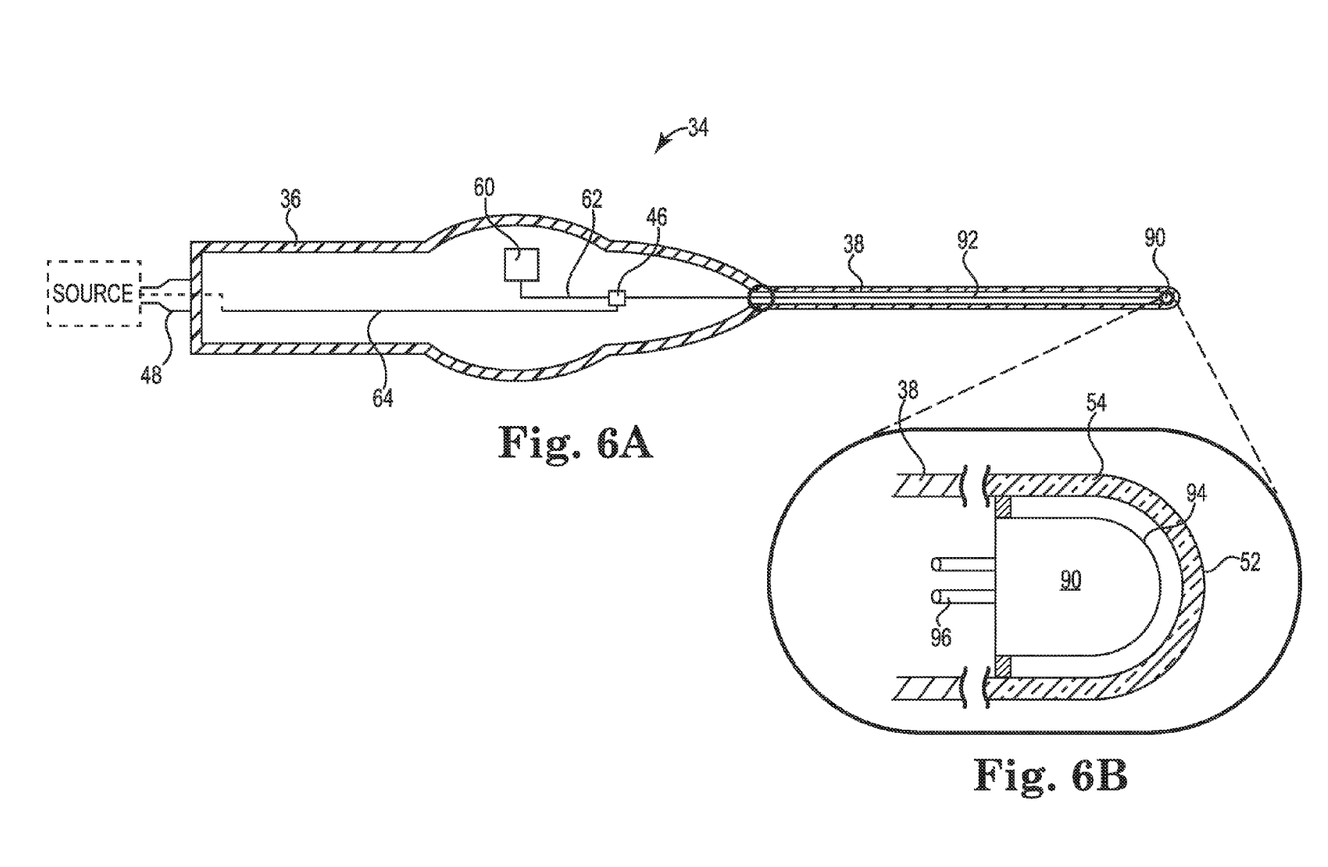
FIG. 6A is a cross-sectional view of the surgical tool illustrated in FIG. 3 provided with one embodiment of a transmitter.
FIG. 6B is a partial cross-sectional view of a distal end portion of a probe and the transmitter of the surgical tool illustrated in FIG. 6A.

FIG. 6A is a cross-sectional view of one embodiment of the tool 34. The switch 46 is appropriately connected to the integrated circuit 60 by electrical connection 62 and to a transmitter 90 by electrical connection 92. In one embodiment, the transmitter 90 is configured to transmit light in the visible spectrum and is provided as a light emitting diode (LED).

FIG. 6B is a partial cross-sectional view of the LED transmitter 90 inside the distal end portion 54 of the probe 38. The LED is available in the colors red, green, yellow, blue, or white. In one embodiment, the LED is provided as a white light LED, either in a constant light output or a flashing LED output. The transmitter 90 is retained within the probe 38 and transmits light from the end 52. In one embodiment, the distal end portion 54 is provided as an optically clear plastic that retains the LED transmitter 90. Light from the LED transmitter 90 travels through the optically clear distal end portion 54 to be visible by an observer.

The LED 90 is configured as a bright (or sunlight readable) light with an output of about 10,000 mcd of light. The LED transmitter 90 is maintained within a bezel 94 with output terminals 96 that electrically couple with the electrical connection 92. The LED transmitter 90 is sized to fit within the inside diameter of the probe 38, and one suitable size for the diameter of the LED transmitter 90 is about 6 mm. One suitable super bright LED is available as the APEM super bright LED available from Digi-Key Corporation, Thief River Falls, Minn.

Figure 7:
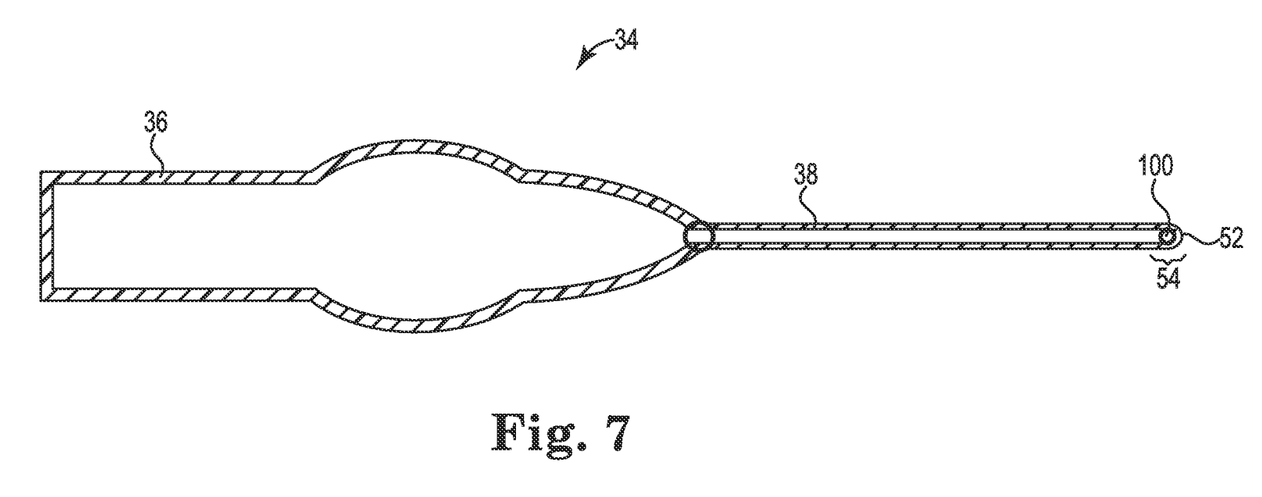
FIG. 7 is a cross-sectional view of the surgical tool illustrated in FIG. 3 provided with one embodiment of a magnetic transmitter.

FIG. 7 is a cross-sectional view of one embodiment of the tool 34. The tool 34 includes the handle 36 attached to the probe 38, where the probe 38 includes a magnetic transmitter 100. In one embodiment, the magnetic transmitter 100 is located inside the distal end portion 54 of the probe 38 and emits a magnetic field that can be sensed with a ferromagnetic material or by another magnet. In one embodiment, the magnetic transmitter 100 is a permanent rare earth magnet that is bonded or otherwise attached inside the distal end portion 54 of the probe 38.

Suitable magnets for the magnetic transmitter 100 include soft or hard ferrite magnets and rare earth magnets. Soft ferrite magnets have a low coercivity in the range of 100-200 kA/m. A permanent hard ferrite magnet is characterized as having a higher coercivity than soft ferrite magnets, with a coercivity from 200-300 kA/m. The relatively high coercivity of the hard ferrite magnet allows the magnet to resist becoming demagnetized. Rare earth magnets are permanent magnets that are formed from the lanthanide elements of metals with ferromagnetic properties. Rare earth magnets have a high coercivity in the range of 450-2000 kA/m and are characterized as having a magnetic strength of 2-5 times greater than ferrite magnets.

Figure 8:
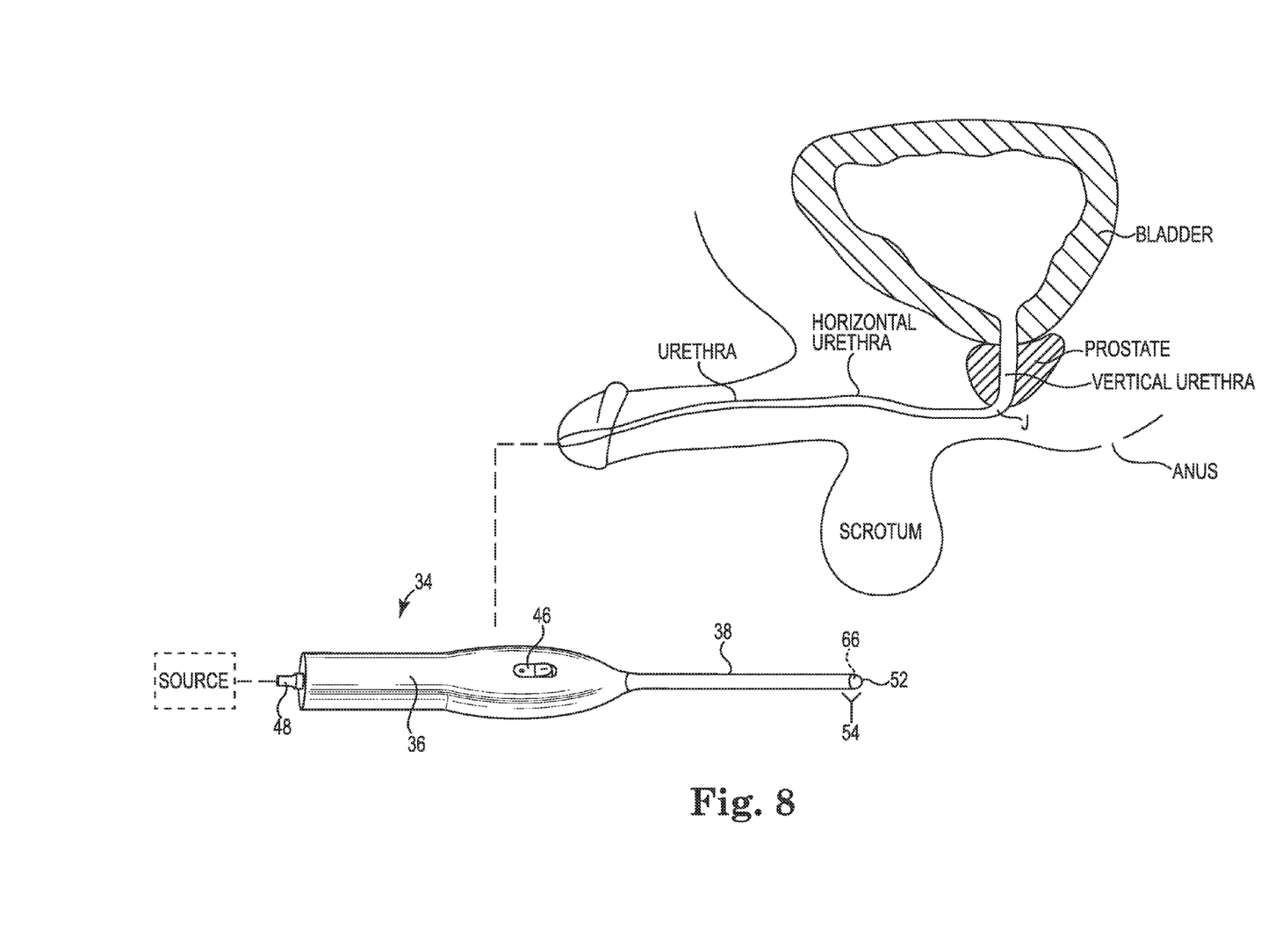
FIG. 8 is a schematic view of male anatomy and the surgical tool illustrated in FIG. 3 ready for insertion into the urethra.

FIG. 8 is a schematic view of the male anatomy and the probe 38. The patient is usually placed in a lithotomy position (the patient is on his back) with the knees spread apart and the feet elevated above the head. The patient is suitably prepared for surgery according to the infection prevention guidelines for open surgical procedures followed by the healthcare facility.

The surgeon orients the penis for insertion of the probe 38. The tool 34 is provided with instructions for use 32 (See FIG. 2) that are followed by the healthcare facility. The probe 38 is sized for insertion into the urethra, is resistant to bending, and is unable to transition past the junction J where the horizontal urethra transitions to the vertical urethra attached to the bladder. The prostate is illustrated between the junction J and the bladder, although it is to be understood that some patients have undergone a prostatectomy and do not have a prostate gland. In any regard, the junction J identifies the bend in the urethra between the horizontal urethra and the vertical urethra that is immediately proximal to the bulbous spongiosis muscle of the bulbar urethra. The surgeon desires to locate the junction J for implantation of an artificial urinary sphincter.

One suitable method of identifying an incision site on a patient includes:

inserting a distal end portion 54 of an intra-urethral probe 38 into a urethra of the patient;

guiding the distal end portion 54 of the intra-urethral probe 38 along a length of the urethra (e.g., horizontal urethra) no farther than a junction J in the urethra, the junction J in the urethra corresponding to a transition in the urethra to a vertical section (e.g., vertical urethra) that is connected to a bladder;

transmitting a signal (see FIG. 9) from the distal end portion 54 of the intra-urethral probe 38 through the urethra; and sensing the signal at a location on a perineal skin surface (the "perineum" of FIG. 9), where the location correlates with the junction J in the urethra.

The surgeon introduces the end 52 of the probe 38 into the urethra and advances the end 52 until resistance it met at the junction J. The end 52 of the probe 38 enters the urethra as far as the junction J where the horizontal urethra bends at the vertical urethra. The end 52 of the probe 38 does not move in a proximal direction into the urethra any farther than the junction J.

Figure 9:
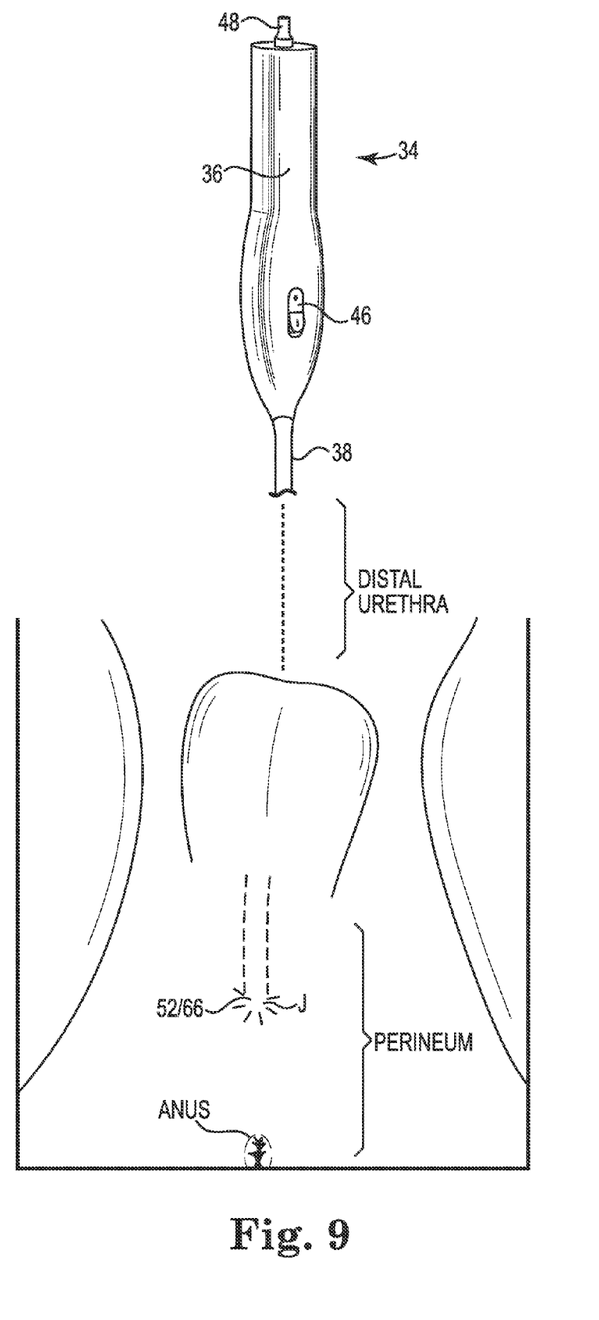
FIG. 9 is a schematic view of the surgical tool illustrated in FIG. 3 inserted into the male urethra and transmitting a signal from the urethra to the surface of the skin to identify an incision site.

FIG. 9 is a schematic view of the probe 38 inserted into the urethra until the distal end 52 locates the junction J. The probe 38 is inside the urethra and is thus under to the skin of the perineum. Activation of the switch 46 energizes the transmitter 66 to produce a vibratory signal that is sensed at the surface of the skin of the perineum. The vibration from the transmitter 66, sensed through the skin, identifies the junction J as the desired location for an incision.

Other signals that are suitable for transmission through the urethra to the skin of the perineum are the light, magnetic, or sound signals described above. In other embodiment described above, activation of the switch 46 energizes a transmitter that transmits a sound signal or light from a LED or a magnetic field from a magnet, and all of these signals can be sensed through the urethral tissue and the skin in a manner that identifies the location of the junction J for forming the incision.

The probe 38 is thus deployed to identify a desired and optimum incision site for placement of an incision through the perineal tissue at the junction J of the urethra. The probe 38 is removed after the incision site is identified, for example by marking the skin with ink or by incising into the skin. Thereafter, the surgeon will place a urinary catheter (such as a Foley catheter) into the bladder through the urethra to drain urine from the bladder.

Figure 10:
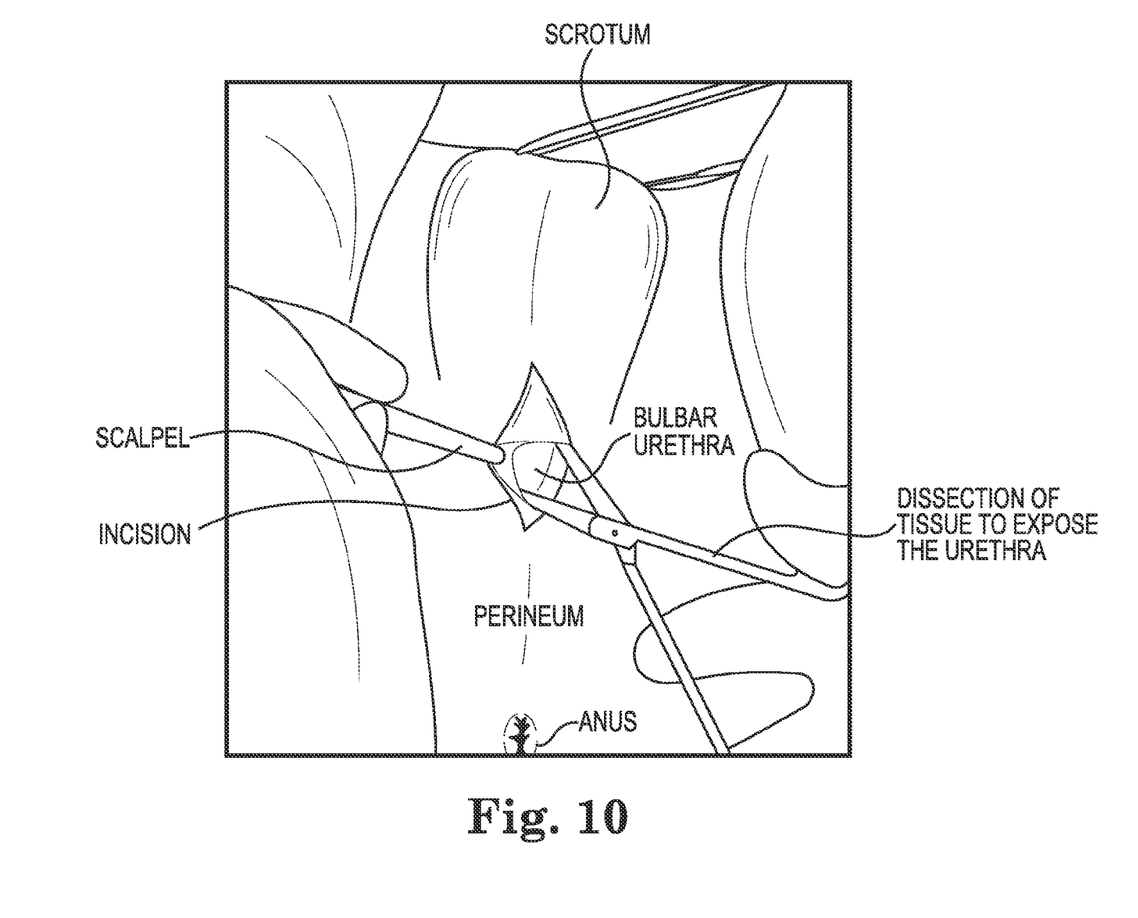
FIG. 10 is a schematic view of tissue dissection at the incision site identified by the tool illustrated in FIG. 3.

FIG. 10 is a schematic view of the scalpel and a dissection tool employed to dissect tissue through the perineum to expose the bulbar urethra.

Figure 11:
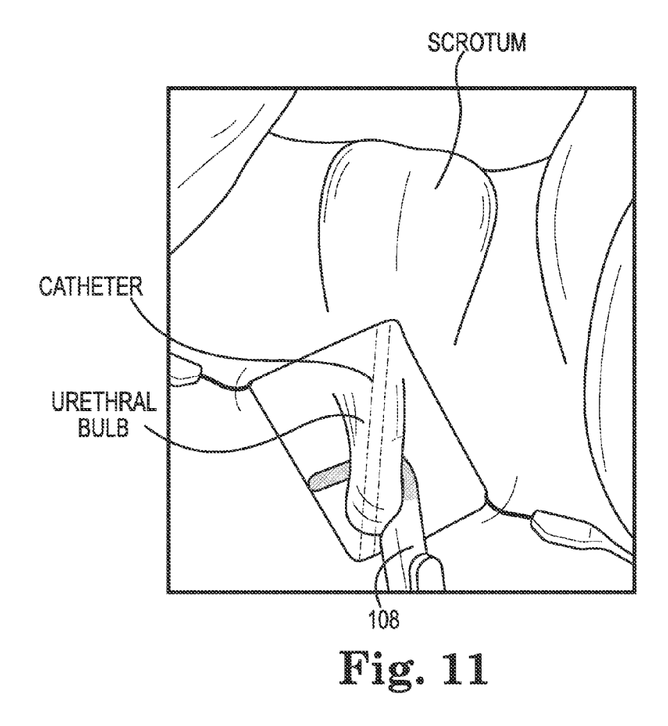
FIG. 11 and FIG. 12 are schematic views of the placement of a cuff of an AUS around a urethra of a patient.

FIG. 11 is a schematic view of the urinary catheter place inside the bladder through the urethra to drain urine from the bladder. The surgeon has dissected tissue away from and around the urethral bulb for the suitable placement of a cuff 108 of the AUS.

Figure 12:
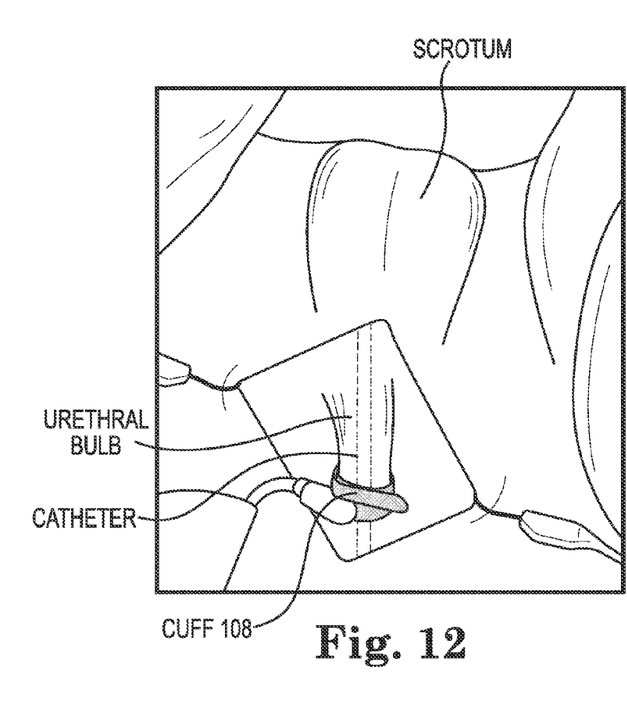

FIG. 12 is a schematic view of the cuff 108 placed around the urethral bulb of the patient.

Embodiments provide a surgical system adapted for identifying an incision site for the placement of an AUS. The system includes an intra-urethral probe having a distal end including a transmitter. Activation of the transmitter produces a signal that can be sensed by the surgeon to identify the location of the distal end of the probe. Introducing the probe and activating the transmitter operates to locate the ideal location for forming an incision during implantation of an artificial sphincter.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A method of identifying a site for a perineal incision on a patient, the method comprising:
    inserting a distal end portion of an intra-urethral probe into a urethra of the patient;
    guiding the distal end portion of the intra-urethral probe along a length of the urethra no farther than a junction in the urethra, the junction in the urethra corresponding to a transition in the urethra to a vertical section that is connected to a bladder;
    transmitting a signal from the distal end portion of the intra-urethral probe through the urethra; and
    sensing the signal at a location on a perineal skin surface to identify a location of the distal end portion of the intra-urethral probe based on the signal, where the location on the perineal skin surface correlates with the location of the distal end portion of the intra-urethral probe and the junction in the urethra.

2. The method of claim 1, comprising sizing the intra-urethral probe to have a length of less than about 16 cm and fabricating the intra-urethral probe to have a rigidity characterized by a flexural modulus between 50,000-200,000 psi.

3. The method of claim 1, comprising providing the intra-urethral probe with an inability to bend and traverse the junction in the urethra between a horizontal section of the urethra and the vertical section that is connected to the bladder.

4. The method of claim 1, wherein transmitting the signal from the distal end portion of the intra-urethral probe through the urethra includes transmitting a vibration from the distal end portion of the intra-urethral probe, through the urethra and tissue to the perineal skin surface.

5. The method of claim 1, wherein transmitting the signal from the distal end portion of the intra-urethral probe through the urethra includes transmitting a magnetic field and sensing the magnetic field with one of a ferromagnetic material and a magnet.

6. The method of claim 1, wherein transmitting the signal from the distal end portion of the intra-urethral probe through the urethra includes transmitting light from the distal end portion of the intra-urethral probe, through the urethra and tissue to the perineal skin surface.

7. The method of claim 1, wherein sensing the signal at the location on the perineal skin surface includes sensing the signal with a sensor, and
    wherein identifying the location of the distal end portion of the intra-urethral probe includes positioning the sensor at the location on the perineal skin surface based on the sensed signal.

8. The method of claim 7,
    wherein the signal is a magnetic signal, and
    wherein the sensor includes a magnet.

9. A method of identifying a site for a perineal incision on a patient, the method comprising:
    providing a kit of parts including a surgical tool and instructions for use of the surgical tool, the surgical tool comprising an intra-urethral probe having a transmitter located at a distal end portion of the intra-urethral probe;
    inserting the distal end portion of the intra-urethral probe into a urethra of the patient;
    guiding the distal end portion of the intra-urethral probe along a length of the urethra no farther than a junction in the urethra, the junction in the urethra corresponding to a transition in the urethra to a vertical section that is connected to a bladder;
    transmitting a signal from the distal end portion of the intra-urethral probe through the urethra; and
    sensing the signal at a location on a perineal skin surface to identify a location of the distal end portion of the intra-urethral probe based on the signal and the location on the perineal skin surface, where the location on the perineal skin surface correlates with the location of the distal end portion of the intra-urethral probe and the junction in the urethra.

10. The method of claim 9, comprising sizing the intra-urethral probe to have a length of less than about 16 cm and fabricating the intra-urethral probe to have a rigidity characterized by a flexural modulus between 50,000-200,000 psi.

11. The method of claim 9, comprising fabricating the intra-urethral probe to resist bending and thus preventing the intra-urethral probe from traversing a curve in the urethra and entering the bladder.

12. A method of identifying a site for a perineal incision on a patient, the method comprising:
    providing a kit of parts including a surgical tool and instructions for use of the surgical tool, the surgical tool comprising an intra-urethral probe having a transmitter located at a distal end portion of the intra-urethral probe;
    inserting the distal end portion of the intra-urethral probe into a urethra of the patient;
    guiding the distal end portion of the intra-urethral probe along a length of the urethra and preventing a distal end of the intra-urethral probe from a bladder;
    transmitting a signal from the distal end portion of the intra-urethral probe through the urethra;
    sensing the signal at a location on a perineal skin surface;
    marking the location on the perineal skin surface; and
    forming an incision at the location on the perineal skin surface.

13. The method of claim 12, comprising fabricating the intra-urethral probe to have a rigidity characterized by a flexural modulus between 50,000-200,000psi.

14. The method of claim 12, wherein transmitting the signal from the distal end portion of the intra-urethral probe through the urethra includes transmitting a vibration from the distal end portion of the intra-urethral probe, through the urethra and tissue to the perineal skin surface.

15. The method of claim 12, wherein transmitting the signal from the distal end portion of the intra-urethral probe through the urethra includes transmitting a magnetic field and sensing the magnetic field with one of a ferromagnetic material and a magnet.

16. The method of claim 12, wherein transmitting the signal from the distal end portion of the intra-urethral probe through the urethra includes transmitting light from the distal end portion of the intra-urethral probe, through the urethra and tissue to the perineal skin surface.

17. The method of claim 12, wherein sensing the signal at the location on the perineal skin surface includes sensing the signal with a sensor, and
   wherein identifying the location of the distal end portion of the intra-urethral probe includes positioning the sensor at the location on the perineal skin surface based on the sensed signal.

18. The method of claim 17,
   wherein the signal is a magnetic signal, and
   wherein the sensor includes a magnet.

\* \* \* \* \*